United States Patent [19]
Von Oepen

[11] Patent Number: 6,068,656
[45] Date of Patent: *May 30, 2000

[54] CORONARY STENT

[75] Inventor: Randolf Von Oepen, Hirrlingen, Germany

[73] Assignee: Jomed Implantate GmbH, Rangendingen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/080,086

[22] Filed: May 15, 1998

[30] Foreign Application Priority Data

May 15, 1997 [DE] Germany ................. 297 08 689 U

[51] Int. Cl.⁷ ........................................ A61F 2/06
[52] U.S. Cl. ........................................ 623/1.17; 623/1.15
[58] Field of Search ................... 623/1.1, 12, 1.15, 623/1.17, 1.3; 606/192, 194, 195

[56] References Cited

U.S. PATENT DOCUMENTS

| | | | |
|---|---|---|---|
| 5,669,932 | 9/1997 | Fischell et al. | 606/198 |
| 5,741,327 | 4/1998 | Frantzen | 623/1 |
| 5,776,183 | 7/1998 | Kanesaka et al. | 623/1 |

*Primary Examiner*—Bruce Snow
*Attorney, Agent, or Firm*—Shinjyu Global IP Counselors, LLP

[57] ABSTRACT

A coronary stent having a tubular, flexible body is disclosed. The body has a wall which has a web structure. The web structure has a plurality of neighboring cells which are defined by webs and which are each connected via joint webs to neighboring cells. The stent has in axial direction first and second cells that differ form one another and are alternately arranged in axial direction of the stent. The identical cells are provided in neighboring fashion in circumferential direction. In a non-expanded state of the stent, the first cells have folded webs at two opposite sides, and in the non-expanded state the second cells are provided at all sides with web portions that are folded and/or placed together.

14 Claims, 2 Drawing Sheets

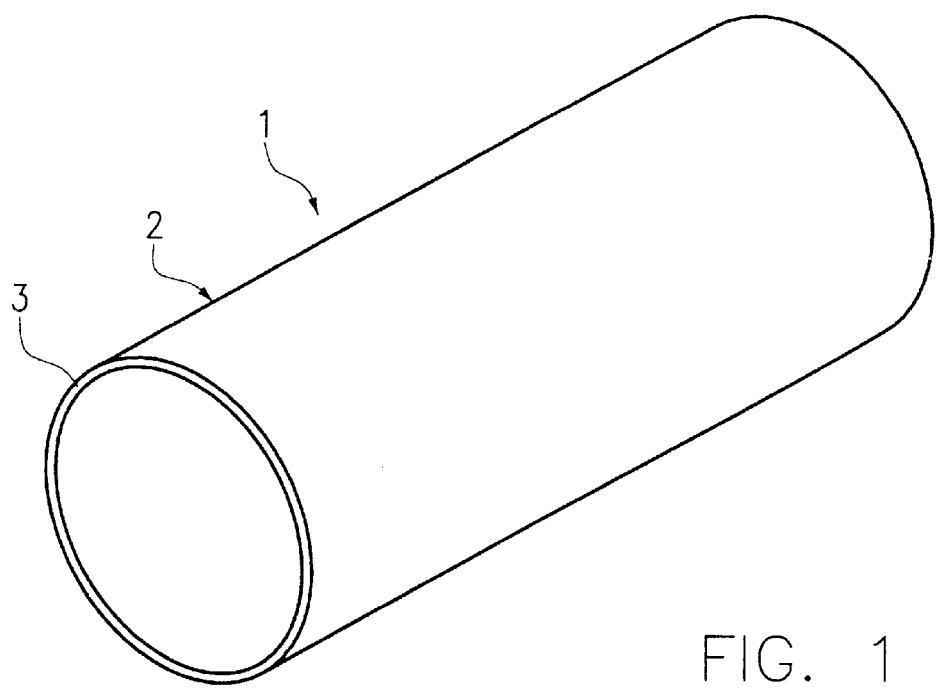
FIG. 1
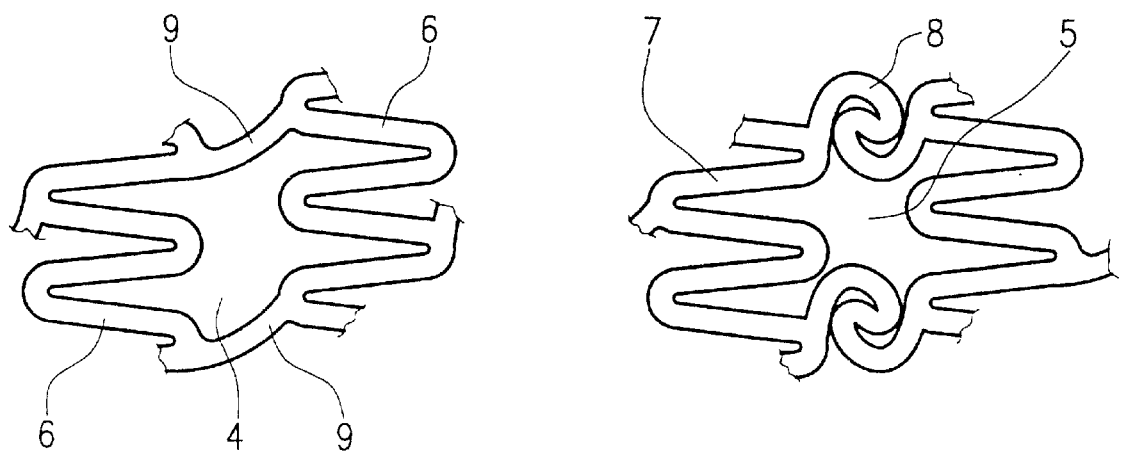
FIG. 3
FIG. 4

CORONARY STENT

FIELD OF THE INVENTION

The present invention relates to a coronary stent comprising a tubular, flexbile body whose wall has a web structure, said web structure comprising a plurality of adjacent cells which are defined by webs and which are each connected via joint webs to adjacent cells.

BACKGROUND OF THE INVENTION

Very different types of coronary stents are already known from the prior art. The stents form a vascular prosthesis made from a physically compatible material. The stent or stent prosthesis is used for expanding blood vessels or also other body orifices and for keeping said vessels in their expanded state. To this end, the stent is positioned in a patient's body in its non-expanded state and is then expanded by suitable means, for instance a balloon catheter. During expansion the individual web portions of the stent are deformed such that the stent permanently remains in its expanded form.

A stent of such a type is, for instance, shown in Utility Model 297 02 671.

When stents are constructed, the fundamental problem arises that these must have a sufficiently small diameter in their non-expanded state to be introducible into and positionable in a patient's body. The stents must be flexible along their longitudinal axis to some degree so as to be able to follow the shapes of, for instance, blood vessels. During expansion the stent must be expanded such that its outer diameter becomes considerably larger. Such an expansion is achieved by deforming the individual web portions in such a manner that no cracks, or the like, are formed.

SUMMARY OF THE INVENTION

It is the object of the present invention to provide a stent of the above-mentioned type which is expandable and, nevertheless, of a simple structure, which can easily be manufactured and safely used.

This object is achieved according to the invention by.

Hence, according to the invention, first and second cells that are movable away from one another are alternately arranged in the axial direction of the stent, identical cells are respectively provided in neighboring fashion in the circumferential direction, in the non-expanded state of the stent the first cells are provided at two opposite sides with folded webs and, in the non-expanded state, the second cells are provided at all sides with web portions that are folded and/or placed together.

The stent of the invention is characterized by several considerable advantages.

In the non-expanded state the alternating arrangement of different cells yields sufficient strength on the one hand and sufficient flexibility on the other hand. Since the webs or web portions of the different cells have different expansion characteristics, the stent can be expanded in a simple and reliable manner. Hence, the different cells permit a corresponding deformation of the webs, so that the formation of cracks or the like can be ruled out.

It has turned out to be particularly advantageous when the folded webs of the first cells have a zig-zag-shaped design, so that these preferably form a tape-like portion extending in circumferential direction. These tape-like portions increase the strength of the stent and also ensure the dimensional stability thereof in the expanded state.

Since the webs or web portions of the second cells have a different design, different expansion characteristics of the webs or web portions are possible. While the zig-zag-shaped web portions are deformable in a manner similar to that of the first cells, the web portions which are placed together in arc-shaped configuration permit a high degree of deformation and expansion. Very long web portions can be provided in a space-saving manner in the non-expanded state owing to the preferably s-shaped arrangement.

The non-folded webs of the first cells are preferably arranged in arc-shaped configuration and parallel to one another, which also leads to a sufficient degree of deformability of the cells and to an increase in stability, in particular in the expanded state.

BRIEF DESCRIPTION OF THE DRAWINGS

The invention shall now be described with reference to an embodiment in conjunction with the drawing, in which:

FIG. 1 is a schematically very simplified illustration of the basic structure of the stent according to the invention;

FIG. 3 is an enlarged illustration of a first cell, and

FIG. 4 is an enlarged illustration of a second cell.

FIG. 1 shows the fundamental structure of an inventive stent 1 which comprises a flexible, tubular body 2 having a wall 3, of which the front side is visible in FIG. 1.

FIG. 2 shows the construction of the web structure of the invention.

DETAILED DESCRIPTION OF THE INVENTION

Figure 2:
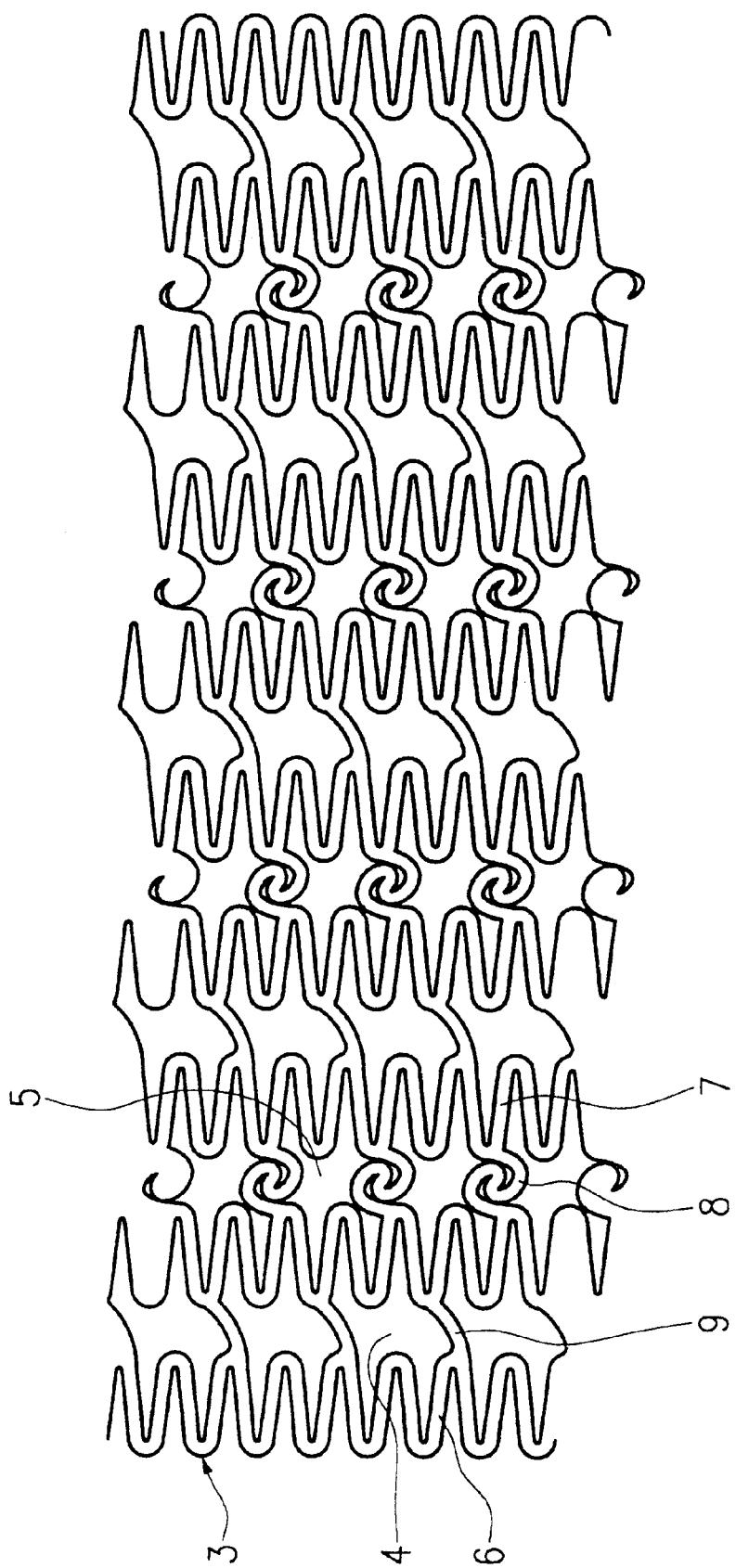
FIG. 2 is an illustration of the web structure of the wall of the stent in the non-expanded state.

As becomes apparent from the figures, rows of first cells 4 and of adjoining second cells 5 are alternately provided in circumferential direction. Each of the first cells 4 are provided at two opposite sides with webs 6 that are arrranged in zig-zag-shaped or v-shaped configuration, while the other sides of the first cells 4 are formed by arc-shaped webs 9 that are parallel to one another.

Shape and design of the second cells 5 differ from those of the first cells 4 by the feature that all webs that define cells 5 are folded or placed together.

As follows from FIG. 4, v-shaped or zig-zag-shaped webs 6 are formed at two opposite sides of the cell 5, while the two other opposite portions have provided thereat webs 8 which are in arc-shaped engagement. Thus, the webs 8 have an s-shaped structure.

Accordingly, as best seen in FIGS. 2–4, coronary stent 1 has a plurality of first cells 4 arranged to form a plurality of first circumferential rows that are axially spaced apart. A plurality of first and second circumferential webs 6 and a plurality of first and second axial webs 9 form the first cells 4. The axial webs 9 are connected to the circumferential webs 6 such that the circumferentially adjacent ones of the first cells 4 share one of the axial webs 9. The first cells 4 have different expansion characteristics from second cells 5. The plurality of second cells 5 are arranged to form a plurality of second circumferential rows that are axially spaced apart and located between the first circumferential rows of first cells 4. Thus, the adjacent second circumferential rows alternate in an axial direction of the tubular coronary stent as seen in FIG. 2. The first and second circumferential webs 6 and third and fourth axial webs 8 form the second cells. The third and fourth axial webs 8 are connected to the first and second circumferential web 6 such that circumferentially adjacent ones of the second cells 5 share one of the axial webs 8.

The coronary stent 1 of the inventive structure is very flexible in the non-expanded state both in the longitudinal direction and in the transverse direction. Arrangement and design of the webs yield good expansion characteristics and also a high degree of dimensional stability in the expanded state.

The inventive stent is made from a physically compatible material, in particular stainless steel. The invention is not limited to the illustrated embodiment. Rather, many variations and modifications are possible within the scope of the invention.

What is claimed is:

1. A coronary stent comprising a tubular, flexible body having a wall formed by a web structure, said web structure comprising: a plurality of first neighboring cells and a plurality of second neighboring cells which are defined by a plurality of circumferential webs and a plurality of axial webs that are connected together such that two of said circumferential webs and two of said axial webs define one of said first and second cells with adjacent ones of said first and second cells sharing one of said circumferential webs, said first and second cells being connected together to form a plurality of circumferentially extending rows of said first cells and a plurality of circumferentially extending rows of said second cells, said first cells differ from said second cells, said rows of said first cells and said rows of said second cells are alternately arranged in axial direction of said stent, said circumferential webs of each of said first and second cells being folded webs that are located at two opposite sides of said first and second cells when said stent is in a non-expanded state, and said axial webs of said second cells being folded webs that are placed together to overlap in a circumferential direction when said stent is in a non-expanded state, said circumferential webs of said first and second cells being arranged to expand in a circumferential direction of said tubular coronary stent when said tubular coronary stent is radially expanded and said axial webs of said second cells being arranged to expand in an axial direction of said tubular coronary stent by expansion of said circumferential webs in the circumferential direction when said tubular coronary stent is radially expanded.

2. The stent according to claim 1, wherein said folded webs of said first cells are arranged in zig-zag shaped fashion.

3. The stent according to claim 1, wherein
said folded webs of said first cells form a plurality of continuous tape portions extending in circumferential directions.

4. The stent according to claim 1, wherein some of said webs of said second cells are folded in different forms.

5. The stent according to claim 1, wherein
two of said webs of said first cells are non-folded webs with an arched shape.

6. The stent according to claim 4, wherein
two of said folded webs of said second cells that are located on opposite sides are configured to be zig-zag shaped and two other of said folded webs of said second cells are placed together in arc-shaped fashion.

7. The stent according to claim 6, wherein the arc-shaped portion is substantially s-shaped.

8. The stent according to claim 7, wherein
two of said webs of said first cells are non-folded webs with an arched shape.

9. The stent according to claim 8, wherein the non-folded webs of said first cells are each made identical and placed parallel to one another.

10. A flexible, tubular coronary stent that is adapted to be expanded from a non-expanded state, comprising:

a plurality of first cells arranged to form a plurality of circumferential rows that are axially spaced apart, each of said first cells being formed by a pair of circumferential webs, and a pair of non-folded axial webs connected to adjacent pairs of said circumferential webs such that circumferentially adjacent ones of said first cells share one of said non-folded axial webs; and a plurality of second cells that expand differently from said first cells, said second cells being arranged to form a plurality of second circumferential rows that are axially spaced apart from each other and located between said first circumferential rows such that said first and second circumferential rows alternate in an axial direction of said tubular coronary stent, said second cells being formed by said circumferential webs and a pair of s-shaped axial webs connected to said circumferential webs such that circumferentially adjacent ones of said second cells share one of said s-shaped axial webs, said circumferential webs being folded in said non-expanded state to expand in a circumferential direction of said tubular coronary stent when said tubular coronary stent is radially expanded, and said s-shaped axial webs being folded to be placed together and overlap in a circumferential direction in said non-expanded state and to expand in an axial direction of said tubular coronary stent by expansion of said circumferential webs in the circumferential direction when said tubular coronary stent is radially expanded.

11. The flexible, tubular coronary stent according to claim 10, wherein
each of said circumferential webs have identical configurations.

12. The flexible tubular coronary stent according to claim 10, wherein
said circumferential webs are configured to be zig-zag shaped.

13. The flexible tubular coronary stent according to claim 10, wherein
said first webs have an arched shape.

14. The flexible tubular coronary stent according to claim 10, wherein
said first axial webs are identical and parallel to one another.

* * * * *